United States Patent [19]

Wilson et al.

[11] Patent Number: 5,872,154
[45] Date of Patent: Feb. 16, 1999

[54] METHOD OF REDUCING AN IMMUNE RESPONSE TO A RECOMBINANT ADENOVIRUS

[75] Inventors: James M. Wilson, Gladwyne; Yiping Yang, Philadelphia; Giorgio Trinchieri, Wynnewood, all of Pa.

[73] Assignees: The Trustees of the University of Pennsylvania; The Wistar Institute of Anatomy & Biology, both of Philadelphia, Pa.

[21] Appl. No.: 394,032

[22] Filed: Feb. 24, 1995

[51] Int. Cl.⁶ .......................... A61K 38/00; A61K 38/20; A61K 38/21; A61K 39/235

[52] U.S. Cl. .................. 514/885; 424/85.2; 424/85.5; 424/154.1; 424/233.1; 424/93.2; 424/93.6; 514/49; 514/50; 514/44; 435/320.1; 435/69.1

[58] Field of Search .............................. 514/44, 50, 885, 514/49; 424/85.2, 154.1, 233.1, 85.5; 435/320.1, 69.1

[56] References Cited

U.S. PATENT DOCUMENTS

| | | |
|---|---|---|
| 4,658,019 | 4/1987 | Kung et al. . |
| 5,017,691 | 5/1991 | Lee et al. . |
| 5,166,320 | 11/1992 | Wu et al. . |
| 5,240,846 | 8/1993 | Collins et al. . |
| 5,290,540 | 3/1994 | Prince et al. . |
| 5,419,900 | 5/1995 | Lane et al. .............................. 424/85.2 |
| 5,457,038 | 10/1995 | Trinchieri et al. . |

FOREIGN PATENT DOCUMENTS

| | | |
|---|---|---|
| 501233 | 9/1992 | European Pat. Off. . |
| 555880 | 8/1993 | European Pat. Off. . |
| 609739 | 8/1994 | European Pat. Off. . |
| WO90/05147 | 5/1990 | WIPO . |
| WO91/18088 | 11/1991 | WIPO . |
| WO92/19266 | 11/1992 | WIPO . |
| WO93/00431 | 1/1993 | WIPO . |
| WO94/12649 | 6/1994 | WIPO . |
| WO94/17832 | 8/1994 | WIPO . |
| WO96/12030 | 4/1996 | WIPO . |
| WO96/12406 | 5/1996 | WIPO . |
| WO96/14061 | 5/1996 | WIPO . |
| WO96/18418 | 6/1996 | WIPO . |

OTHER PUBLICATIONS

Wilson, C. & Kay, M. A., Nature Medicine, vol. 1, pp. 887–889, Sep. 1995.
Tahara & Lotze, Gene Therapy, vol. 2, pp. 96–106, Mar. 1995.
Coghlan, Focus, vol. 148, pp. 14–15, Nov. 25, 1995.
Brown, "News Media, Researchers 'Oversold' Gene Therapy . . . Says", The Washington Post, Dec. 8, 1995.
Mulligan, Science, vol. 260, pp. 926–930, May 14, 1993.
Kremer & Perricaudet, British Medical Bulletin, vol. 51, pp. 31–44, Jan. 1995.
Orkin & Motulsky, Report and Recommendations of the Panel to Assess . . . Gene Therapy, Dec. 7, 1995.
Losordo et al., Circulation, vol. 89, pp. 785–792, Feb. 1994.
Harada et al., Journal of Neuro–Oncology, vol. 22, pp. 221–225, 1994.
Raz et al., Proceedings of the National Academy of Sciences, vol. 90, pp. 4523–4527, May 1993.
Y. Yang et al, "Transient Immune Blockade Prevents Formation of Neutralizing Antibody to Recombinant Adenovirus and Allows Repeated Gene Transfer to Mouse Liver", *Gene Therapy*, 3(5):412–420 (1996) [Yang IV].
Y. Yang et al, "Recombinant IL–12 Prevents Formation of Blocking IgA Antibodies to Recombinant Adenovirus and Allows Repeated Gene Therapy to Mouse Lung", *Nature Medicine*, 1(9):890–893 (Sep., 1995) [Yang V].
M. Lee et al, "The Constitutive Expression of the Immunomodulatory gp19k Protein in E1–, E3– Adenoviral Vectors Strongly Reduces the Host Cytotoxic T Cell Response Against the Vector", *Gene Therapy*, 2:256–262 (Jun., 1995).
B. Trapnell et al, "Pharmacologic Immunomodulation Enhances Repeated in vivo Adenovirus–Mediated Gene Transfer", *J. Cell. Biochem.*, 21A:415, Abstract No. C6–449 (Apr., 1995).
B. Fang et al, "Gene Therapy for Hemophilia B: Host Immunosuppression Prolongs the Therapeutic Effect of Adenovirus–Mediated Factor IX Expression", *Human Gene Therapy*, 6:1039–1044 (Aug., 1995).
J. Zabner et al, "Safety and Efficacy of Repetitive Adenovirus–Mediated Transfer of CFTR cDNA to Airway Epithelia of Primates and Cotton Rats", *Nature Genetics*, 6:75–83 (Jan., 1994).
A. Elshami et al, "The Role of Immunosupression in the Efficacy of Cancer Gene Therapy Using Adenovirus Transfer of the Herpes Simplex Thymidine Kinase Gene", *Annals of Surgery*, 222(3):298–310 (Sep., 1995).
J. Wilson, "Gene Therapy for Cystic Fibrosis: Challenges and Future Directions", *J. Clin. Invest.*, 96:2567–2554 (Dec., 1995) [Wilson V].
E. Marshall, "Gene Therapy's Growing Pains", *Science*, 269:1050–1055 (Aug., 1995).
Y. Dai et al, "Cellular and Humoral Immune Responses to Adenoviral Vectors Containing Factor IX Gene: Tolerization of Factor IX and Vector Antigens Allows for Long–Term Expression", *Proc. Natl. Acad. Sci. USA*, 92:1401–1405 (Feb., 1995).
J. Engelhardt et al, "Direct Gene Transfer of Human CFTR into Human Bronchial Epithelia of Xenografts with E1–Deleted Adenoviruses", *Nature Genetics*, 4:27–34 (May, 1993) [Engelhardt IV].
J. Wilson, "Cystic Fibrosis—Vehicles for Gene Therapy", *Nature*, 365:691–692 (Oct. 21, 1993) [Wilson I].

(List continued on next page.)

*Primary Examiner*—Jasemine C. Chambers
*Assistant Examiner*—Jill Schmuck
*Attorney, Agent, or Firm*—Howson and Howson

[57] ABSTRACT

A method of reducing an immune response to a recombinant adenovirus which involves co-administration of the recombinant adenovirus and a selected immune modulator. The immune modulator functions by inhibiting the formation of neutralizing antibodies and/or reducing CTL killing of the virally infected cells. The method additionally encompasses the step of re-administering the recombinant adenovirus.

21 Claims, 3 Drawing Sheets

OTHER PUBLICATIONS

J. Wilson et al, "Correction of the Genetic Defect in Hepatocytes from the Watanabe Heritable Hyperlipidemic Rabbit", *Proc. Natl. Acad. Sci. USA,* 85:4421–4425 (Jun., 1988) [Wilson II].

J. Wilson et al, "Research Article—Transplantation of Allogeneic Hepatocytes into LDL Receptor Deficient Rabbits Leads to Transient Improvement in Hypercholesterolemia", *Clin. Bio.,* 3:21–26 (Spring, 1991) [Wilson III].

J. Wilson et al, "A Novel Mechanism for Achieving Transgene Persistence in vivo after Somatic Gene Transfer into Hepatocytes", *J. Biol. Chem.,* 267(16):11483–11489 (Jun. 5, 1992) [Wilson IV].

K. Kozarsky et al, "In Vivo Correction of Low Density Lipoprotein Receptor Deficiency in the Watanabe Heritable Hyperlipidemic Rabbit with Recombinant Adenoviruses", *J. Biol. Chem.,* 269(18):13695–13702 (May 6, 1994) [Kozarsky I].

K. Kozarsky et al, "Adenovirus–Mediated Correction of the Genetic Defect in Hepatocytes from Patients with Familial Hypercholesterolemia", *Somatic Cell and Molecular Genetics,* 19(5):449–458 (Sep., 1993) [Kozarsky II].

K. Kozarsky et al, "Gene Therapy: Adenovirus Vectors", *Curr. Opin. Genet. Devel.,* 3:499–503 (Mar., 1993) [Kozarsky III].

Y. Yang et al, "MHC Class I–Restricted Cytotoxic T Lymphocytes to Viral Antigens Destroy Hepatocytes in Mice Infected with E1–Deleted Recombinant Adenoviruses", *Immunity,* 1:433–442 (Aug., 1994) [Yang I].

Y. Yang et al, "Cellular Immunity to Viral Antigens Limits E1–Deleted Adenoviruses for Gene Therapy", *Proc. Natl. Acad. Sci. USA,* 91:4407–4411 (May, 1994) [Yang II].

Y. Yang et al, "Inactivation of E2a in Recombinant Adenoviruses Improves the Prospect for Gene Therapy in Cystic Fibrosis", *Nature Genetics,* 7:362–369 (Jul., 1994) [Yang III].

J. Goldstein et al, "Familial Hypercholesterolemia", in *The Metabolic Basis of Inherited Disease,* Chapter 48, 6th ed., C.R. Scrivers et al (eds), McGraw–Hill Information Services Co., New York, pp. 1215–1250 (1989) [Goldstein I].

J. Goldstein et al, "Defective Lipoprotein Receptors and Atherosclerosis—Lessons from an Animal Counterpart of Familial Hypercholesterolemia", *New Engl. J. Med.,* 309(5):288–296 (Aug. 4, 1983) [Goldstein II].

J. Goldstein et al, "Disorders of the Biogenesis and Secretion of Lipoproteins", in *The Metabolic Basis of Inherited Disease,* Chapter 44B, 6th ed., C.R. Scrivers et al (eds), McGraw–Hill Information Services Co., New York, pp. 1155–1156 (1989) [Goldstein III].

S. Ishibashi et al, "Hypercholesterolemia in Low Density Lipoprotein Receptor Knockout Mice and its Reversal by Adenovirus–Mediated Gene Delivery", *J. Clin. Invest.,* 92:883–893 (Aug., 1993) [Ishibashi I].

S. Ishibashi et al, "Massive Xanthomatosis and Atherosclerosis in Cholesterol–fed Low Density Lipoprotein Receptor–negative Mice", *J. Clin. Invest.,* 93:1885–1893 (May, 1994) [Ishibashi II].

M. Gafvels et al, "Cloning of a cDNA Encoding a Putative Human Very Low Density Lipoprotein/Apolipoprotein E Receptor and Assignment of the Gene to Chromosome 9pter–p266", *Somatic Cell and Molecular Genetics,* 19(6):557–569 (Sep., 1993) [Gafvels I].

M. Gafvels et al, "Cloning of a Complementary Deoxyribonucleic Acid Encoding the Murine Homolog of the Very Low Density Lipoprotein/Apolipoprotein–E Receptor: Expression Pattern and Assignment of the Gene to Mouse Chromosome 19", *Endocrinology,* 135(1):387–394 (Jul., 1994) [Gafvels II].

S. Takahashi et al, "Rabbit Very Low Density Lipoprotein Receptor: A Low Density Lipoprotein Receptor–Like Protein with Distinct Ligand Specificity", *Proc. Natl. Acad. Sci. USA,* 89:9252–9256 (Oct., 1992).

J. Engelhardt et al, "Ablation of E2A in Recombinant Adenoviruses Improves Transgene Persistence and Decreases Inflammatory Response in Mouse Liver", *Proc. Natl. Acad. Sci. USA,* 91:6196–6200 (Jun., 1994) [Engelhardt I].

J. Engelhardt et al, "Adenovirus–Mediated Transfer of the CFTR Gene to Lung of Nonhuman Primates: Biological Efficacy Study", *Human Genet. Ther.,* 4:759–769 (Dec., 1993) [Engelhardt II].

J. Engelhardt et al, "Prolonged Transgene Expression in Cotton Rat Lung with Recombinant Adenoviruses Defective in E2a", *Human Gene Ther.,* 5:1217–1229 (Oct., 1994) [Engelhardt III].

Y. Watanabe, "Serial Inbreeding of Rabbits with Hereditary Hyperlipidemia (WHHL–Rabbit)", *Atherosclerosis,* 36:261–268 (1980).

K. Tanzawa et al, "WHHL–Rabbit: A Low Density Lipoprotein Receptor–Deficient Animal Model for Familial Hypercholesterolemia", *FEBS Letters,* 118(1):81–84 (Aug., 1980).

M Horwitz, "Adenoviridae and Their Replication", *Virology,* 2d edition, ed. B. N. Fields, Raven Press, Ltd., New York, Chapter 60, pp. 1679–1721 (1990).

M. Grossman et al, "Towards Liver–Directed Gene Therapy: Retrovirus–Mediated Gene Transfer into Human Hepatocytes", *Som. Cell. and Mol. Gen.,* 17(6):601–607 (Nov., 1991).

M. Boshart et al, "A Very Strong Enhancer is Located Upstream of an Immediate Early Gene of Human Cytomegalovirus", *Cell,* 41:521–530 (Jun., 1985).

C. Wu et al, "Targeting Genes: Delivery and Persistent Expression of a Foreign Gene Driven by Mammalian Regulatory Elements in vivo", *J. Biol. Chem.,* 264(29):16985–16987 (Oct. 15, 1989).

K. Fisher et al, "Biochemical and Functional Analysis of an Adenovirus–Based Ligand Complex for Gene Transfer", *Biochem. J.,* 299:49–58 (Apr. 1, 1994).

C. Laughlin et al, "Cloning of Infectious Adeno–associated Virus Genomes in Bacterial Plasmids", *Gene,* 23:65–73 (Jul., 1983).

J. Price et al, "Lineage Analysis in the Vertebrate Nervous System by Retrovirus–mediated Gene Transfer", *Proc. Natl. Acad. Sci. USA,* 84:156–160 (Jan., 1987).

T. Kost et al, "The Nucleotide Sequence of the Chick Cytoplasmid beta–actin Gene", *Nucl. Acids Res.,* 11(23):8287–8301 (Dec. 11, 1983).

J. Schreiber et al, "Recombinant Retroviruses Containing Novel Reporter Genes", *BioTechniques,* 14(5):818–823 (May, 1993).

J. Riordan et al, "Identification of the Cystic Fibrosis Gene: Cloning and Characterization of Complementary DNA", *Science,* 245:1066–1073 (Sep. 8, 1989).

M. Brown et al, "A Receptor–Mediated Pathway for Cholesterol Homeostasis", *Science,* 232:34–46 (Apr. 4, 1986).

T. Yamamoto et al, "The Human LDL Receptor: A Cysteine–Rich Protein with Multiple Alu Sequences in its mRNA", *Cell,* 39:27–38 (Nov., 1984).

R. Samulski et al, "Helper–Free Stocks of Recombinant Adeno–Associated Viruses: Normal Integration does not Require Viral Gene Expression", *J. Virol.,* 63(9):3822–3828 (Sep., 1989).

T. Shenk et al, "Genetic Analysis of Adenoviruses", *Current Topics in Microbiol. and Immunol.,* 111:1–39 (1984).

P. Hearing et al, "Identification of a Repeated Sequence Element Required for Efficient Encapsidation of the Adenovirus Type 5 Chromosome", *J. Virol.,* 61(8):2555–2558 (Aug., 1987).

M. Grable et al, "Adenovirus Type 5 Packaging Domain is Composed of a Repeated Element that is Functionally Redundant", *J. Virol.,* 64(5):2047–2056 (May, 1990) [Grable I].

M. Grable et al, "cis and trans Requirements for the Selective Packaging of Adenovirus Type 5 DNA", *J. Virol.,* 66(2):723–731 (Feb., 1992) [Grable II].

F. Wittmaack et al, "Localization and Regulation of the Human Very Low Density Lipoprotein/Apolipoprotein–E Receptor: Trophoblast Expression Predicts a Role for the Receptor in Placental Lipid Transport", *Endocrinol.,* 136(1):340–348 (Jan., 1995).

M. Rosenfeld et al, "In Vivo Transfer of the Human Cystic Fibrosis Transmembrane Conductance Regulator Gene to the Airway Epithelium", *Cell,* 68:143–155 (Jan. 10, 1992).

J. Logan et al, "Adenovirus Tripartite Leader Sequence Enhances Translation of mRNAs Late After Infection", *Proc. Natl. Acad. Sci. USA,* 81:3655–3659 (Jun., 1984).

P. Van Der Vliet et al, "Thermolabile DNA Binding Proteins from Cells Infected with a Temperature–Sensitive Mutant of Adenovirus Defective in Viral DNA Synthesis", *J. Virol.,* 15(2):348–354 (Feb., 1975).

P. Scott, "IL–12: Initiation Cytokine for Cell–Mediated Immunity", *Science,* 260:496–497 (Apr., 1993).

R. Manetti et al, "Natural Killer Cell Stimulatory Factor (Interleukin 12 [IL–12]) Induces T Helper Type 1 (Th1)–specific Immune Responses and Inhibits the Development of IL–4–Producing Th Cells", *J. Exp. Med.,* 177:1199–1204 (Apr., 1993).

A. D'Andrea et al, "Production of Natural Killer Cell Stimulatory Factor (Interleukin 12) by Peripheral Blood Mononuclear Cells", *J. Exp. Med.,* 176:1387–1398 (Nov., 1992).

S. Morris et al, "Effects of IL–12 on in Vivo Cytokine Gene Expression and Ig Isotype Selection", *J. Immunol.,* 152:1047–1056 (Feb., 1994).

F. Heinzel et al, "Recombinant Interleukin 12 Cures Mice Infected with Leishmania major", *J. Exp. Med.,* 177:1505–1509 (May, 1993).

T. Yokota et al, "Isolation and Characterization of a Human Interleukin cDNA Clone, Homologous to Mouse B–Cell Stimulatory Factor 1, that Expresses B–cell– and T–cell–Stimulating Activities", *Proc. Natl. Acad. Sci. USA,* 83:5894–5898 (Aug., 1986).

F. Durie et al, "The Role of CD40 in the Regulation of Humoral and Cell–Mediated Immunity", *Immunol. Today,* 15(9):406–410 (Sep., 1994).

J. Cohen, "Naked DNA Points Way to Vaccines", *Science,* 259:1691–1692 (Mar. 19, 1993).

A. McKnight et al, "Effects of IL–12 on Helper T Cell–Dependent Immune Responses in Vivo", *J. Immunol.,* 152:2172–2179 (Mar., 1994).

L. Afonso et al, "The Adjuvant Effect of Interleukin–12 in a Vaccine Against Leishmania major", *Science,* 263:235–237 (Jan., 1994).

J. Sypek et al, "Resolution of Cutaneous Leishmaniasis: Interleukin 12 Initiates a Protective T Helper Type 1 Immune Response", *J. Exp. Med.,* 177:1797–1802 (Jun., 1993).

C–S. Hsieh et al, "Development of TH1 CD4+ T Cells Through IL–12 Produced by Listeria–Induced Macrophages", *Science,* 260:547–549 (Apr., 1993).

S. Chan et al, "Induction of Interferon gamma Production by Natural Killer Cell Stimulatory Factor: Characterization of the Responder Cells and Synergy with Other Inducers", *J. Exp. Med.,* 173:869–879 (Apr., 1991).

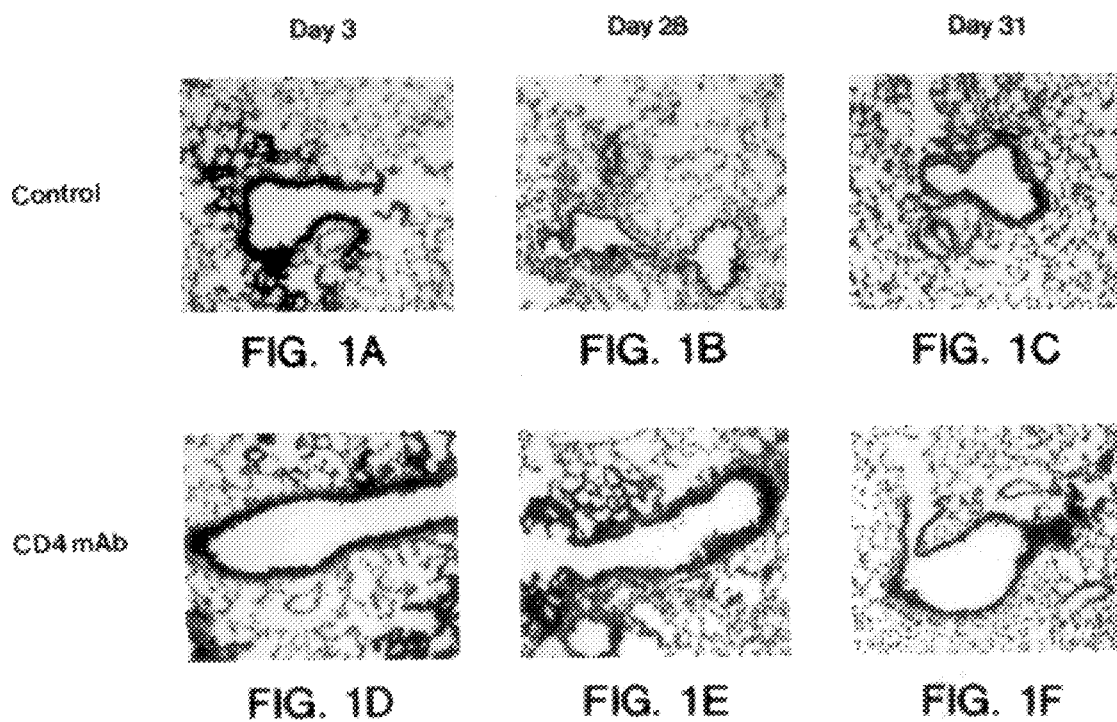

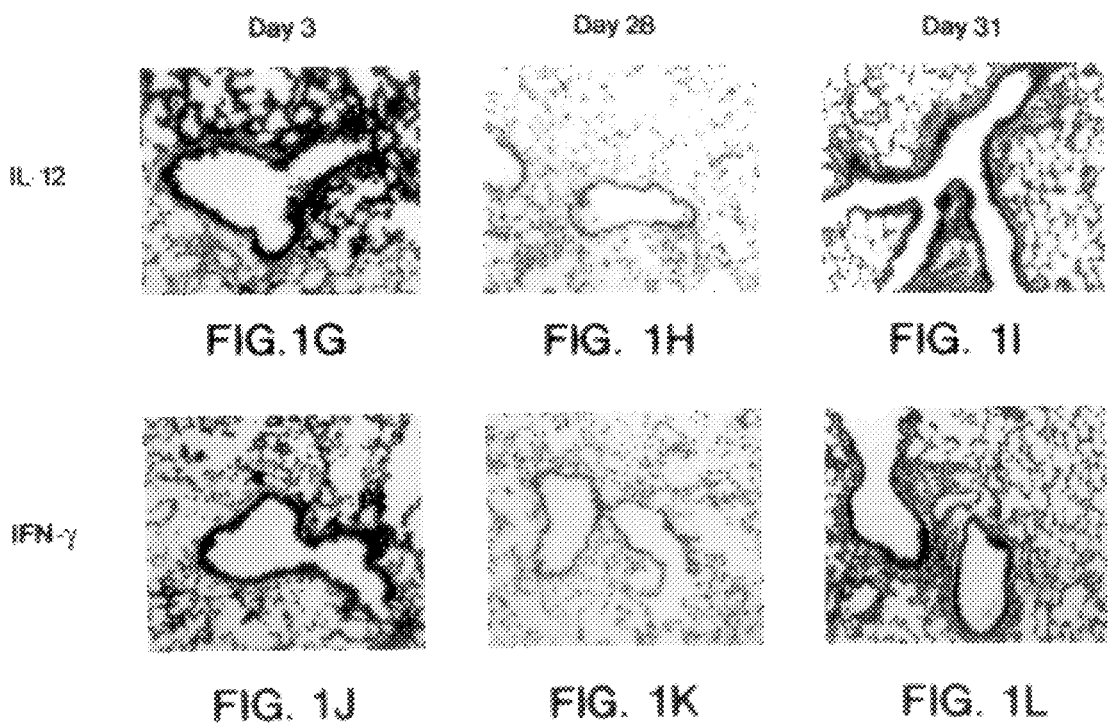

METHOD OF REDUCING AN IMMUNE RESPONSE TO A RECOMBINANT ADENOVIRUS

This invention was supported by the National Institutes of Health Grant No. DK 47757-02 and AI 39412-02. The United States government has certain rights in this invention.

FIELD OF THE INVENTION

The present invention relates generally to gene therapy, and more specifically, to methods of administering viral vectors used in gene therapy.

BACKGROUND OF THE INVENTION

Recombinant adenoviruses have emerged as attractive vehicles for in vivo gene transfer to a wide variety of cell types. The first generation vectors, which are rendered replication defective by deletion of sequences spanning E1, are capable of highly efficient in vivo gene transfer into nondividing target cells [M. Kay et al, *Proc. Natl. Acad. Sci. USA*, 91:2353 (1994); S. Ishibashi et al, *J. Clin. Invest.*, 92:883 (1993); B. Quinn et al, *Proc. Natl. Acad. Sci. USA*, 89:2581 (1992); M. Rosenfeld et al, *Cell*, 68:143 (1992); and R. Simon et al, *Hum. Gene Thera.*, 4:771 (1993)].

Immune responses of the recipient to the viral vector, the transgene carried by the vector, and the virus infected cells have emerged as recurring problems in the initial application of this technology to animals and humans. In virtually all models, expression of the transgene is transient and associated with the development of pathology at the site of gene transfer [M. Kay et al, cited above; S. Ishibashi et al, cited above; B. Quinn et al, cited above; M. Rosenfeld et al, cited above; and R. Simon et al, cited above]. The transient nature of the effect of recombinant adenoviruses in most situations is the development of cellular immune responses to the virus-infected cells and their elimination. Antigenic targets for immune mediated clearance are viral proteins expressed from the recombinant viral genome and/or the product of the transgene. Studies in a variety of models suggest that first generation vectors express viral proteins in addition to the transgene which collectively activate cytotoxic T lymphocytes (CTL) leading to the destruction of the virus infected cells [Y. Dai et al, *Proc. Natl. Acad. Sci. USA*, (in press); Y. Yang et al, *Proc. Natl. Acad. Sci. USA*, 91:4407 (1994); and Y. Yang et al, *Immunity*, 1:433 (1994)]. This problem is potentially overcome through the development of second generation recombinant viruses [Y. Yang et al, *Nat. Genet.*, 7:363 (1994); and J. Engelhardt et al, *Hum. Gene Thera.*, 5:1217 (1994)].

The other limitation of recombinant adenoviruses for gene therapy has been the difficulty in obtaining detectable gene transfer upon a second administration of virus. This limitation is particularly problematic in the treatment of chronic diseases, such as cystic fibrosis, that will require repeated therapies to obtain life-long genetic reconstitution. Diminished gene transfer following a second therapy has been demonstrated in a wide variety of animal models following intravenous or intratracheal delivery of virus [T. Smith et al, *Gene Thera.*, 5:397 (1993); S. Yei et al, *Gene Thera.*, 1:192 (1994); K. Kozarsky et al, *J. Biol. Chem.*, 269:13695 (1994)]. In each case, resistance to repeat gene therapy was associated with the development of neutralizing anti-adenovirus antibody.

There remains a need in the art for a method of improving the efficiency of gene transfer during repeated administrations of viral gene therapy.

SUMMARY OF THE INVENTION

The present invention provides a method of performing gene therapy which results in a reduced immune response to the viral vector used to accomplish the therapy. The method involves co-administering with a gene therapy viral vector a selected immune modulator, which can substantially reduce the occurrence of a neutralizing antibody response directed against the vector itself and/or cytolytic T cell elimination of the vector, particularly where readministration of the recombinant virus is desired. According to this method the immune modulator may be administered prior to, or concurrently with, the viral vector bearing the transgene to be delivered.

Other aspects and advantages of the present invention are described further in the following detailed description of the preferred embodiments thereof.

BRIEF DESCRIPTION OF THE DRAWINGS

FIG. 1A is an alkaline phosphatase histochemical stain of lung tissue of C57BL-6 mice adenovirus-infected on day 0 as described in Example 2 (magnification×100) depicting the staining of lung tissue from normal mice ("control") necropsied on day 3.

FIG. 1B is a stain from control mice immunized as in FIG. 1A, and necropsied on day 28.

FIG. 1C is a stain from control mice, immunized as in FIG. 1A, and necropsied on day 31 following reinfection with lacZ-containing adenovirus vector on day 28.

FIG. 1D is a stain on day 3 of lung tissue from mice immunized as in FIG. 1A, and depleted on days −3, 0, and +3 of CD4$^+$ cells with mAb ("CD4 mAb").

FIG. 1E is a stain on day 28 of CD4 mAb mice immunized as in FIG. 1A.

FIG. 1F is a stain on day 31 of CD4 mAb mice immunized as in FIG. 1A.

FIG. 1G is a stain of lung tissue from mice immunized as in FIG. 1A, and treated with IL-12 on days 0 and +1 ("IL-12") and necropsied on day 3.

FIG. 1H is a stain on day 28 of IL-12 mice immunized as in FIG. 1A.

FIG. 1I is a stain on day 31 of IL-12 mice immunized as in FIG. 1A.

FIG. 1J is a stain of lung tissue from mice immunized as in FIG. 1A and treated with IFN-γ on days 0 and +1 ("IFN-γ") and necropsied on day 3.

FIG. 1K is a stain on day 28 of IFN-γ mice immunized as in FIG. 1A.

FIG. 1L is a stain on day 31 of IFN-γ mice, immunized as in FIG. 1A.

DETAILED DESCRIPTION OF THE INVENTION

Figure 2A:
FIG. 2A is a graph summarizing neutralizing antibody titer present in BAL samples of C57BL-6 mice adenovirus-infected on day 0 and necropsied on day 28 as described in Example 2. Control represents normal mice ("control"); CD4 mAB represents CD4+ depleted mice; IL-12 represents IL-12 treated mice and IFN-γ represent IFN-γ treated mice as described for FIGS. 1A through 1L.

The present invention provides a method for improving an individual's ability to tolerate repeated administrations of gene therapy viral vectors. This method involves administering to an individual a suitable amount of a preferably short-acting, immune modulator, either concurrently with, or before or after administration of a recombinant gene therapy viral vector used to deliver a therapeutic transgene desired for gene therapy.

I. Immune Modulators

The selected immune modulator is defined herein as an agent capable of inhibiting the formation of neutralizing antibodies directed against the recombinant viral vector or capable of inhibiting cytolytic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$ cells and CTLs to reduce the occurrence of CTL elimination of the vector.

Immune modulators for use in inhibiting neutralizing antibody formation according to this invention are selected based on the determination of the immunoglobulin subtype of any neutralizing antibody produced in response to the adenovirus vector. The neutralizing antibody which develops in response to administration of a gene therapy viral vector is frequently based on the identity of the virus, the identity of the transgene, what vehicle is being used to deliver the vector and/or the location of delivery.

For example, the subset of T helper cells designated $T_H2$ is generally responsible for interfering with the efficient transfer of genes administered during gene therapy. This is particularly true when the viral vector is adenovirus-based. More particularly, the inventors have determined that neutralizing antibodies of the subtypes, IgG1 and IgA, which are dependent upon the interaction between $T_H2$ cells and B cells, appear to be the primary cause of major neutralizing antibodies against adenoviral vectors. Administration of adenoviral vectors via the lungs generally induces production of IgA neutralizing antibody. Administration of adenoviral vectors via the blood generally induces $IgG_1$ neutralizing antibody. Thus, when an adenovirus-based viral vector is used in gene therapy, this $T_{H2}$-dependent immune response interferes with transfer of the therapeutic transgene.

The identity of the neutralizing antibody for any specific gene therapy recombinant viral vector is readily determined in trials of each individual vector in animal models.

Thus, where the neutralizing antibody is a $T_{H2}$ mediated antibody, such as IgA or $IgG_1$, the immune modulator selected for use in this method suppresses or prevents the interaction of $T_{H2}$ with B cells. Alternatively, if the neutralizing antibody is a $T_{H1}$, mediated antibody, such as $IgG_{2A}$, the immune modulator desirably suppresses or prevents the interaction of $T_{H1}$ with B cells.

Where, the reduction of CTL elimination of the viral vectors is desired, the immune modulator is selected for its ability to suppress or block CD4+$T_{H1}$ cells to permit prolonged residence of the viral vector in vivo.

A desirable immune modulator for use in this method which selectively inhibits the CD4+T cell subset $T_{H2}$ function at the time of primary administration of the viral vector includes interleukin-12, which enhances antigen specific activity of $T_{H1}$, cells at the expense of the $T_{H2}$ cell function [see, e.g., European Patent Application No. 441,900; P. Scott, *science*, 260:496 (1993); R. Manetti et al, *J. Exp. Med.*, 177:1199 (1993); A. D'Andrea et al, *J. Exp. Med.*, 176:1387 (1992)]. IL-12 for use in this method is preferably in protein form. Human IL-12 may be recombinantly produced using known techniques or may be obtained commercially. Alternatively, it may be engineered into a viral vector and expressed in a target cell in vivo or ex vivo.

Another selected immune modulator which performs the same function is gamma interferon [S. C. Morris et al, *J. Immunol.*, 1:1047 (1994); F. P. Heinzel et al, *J. Exy. Med.*, 177:1505 (1993)]. IFN-γ partially inhibits IL-4 stimulated activation of $T_{H2}$. γIFN may also be obtained from a variety of commercial sources. Alternatively, it may be engineered into a viral vector and expressed in a target cell in vivo or ex vivo by resorting to known genetic engineering techniques.

Preferably, such cytokine immune modulators are in the form of human recombinant proteins. These proteins may be produced by methods extant in the art. It is also anticipated that active peptides, fragments, subunits or analogs of IL-12 or gamma interferon which share the $T_{H2}$ inhibitory function of these proteins, will also be useful in this method when the neutralizing antibodies are $T_{H2}$ mediated.

A desirable immune modulator for use in this method which selectively inhibits the CD4+ T cell subset $T_{H1}$ function at the time of primary administration of the viral vector includes interleukin-4, which enhances antigen specific activity of $T_{H2}$ cells at the expense of the $T_{H1}$ cell function [see, e.g., Yokota et al, *Proc. Natl. Acad. Sci., USA*, 83:5894–5898 (1986); U.S. Pat. No. 5,017,691].

Still other immune modulators which inhibit the $T_H$ cell function may also be employed in this method. Among such modulators are agents that specifically inhibit or deplete CD4+ cells, for example, by antibody to the CD4 protein. Among such agents include anti-T cell antibodies, such as anti-OKT 3+ [see, e.g., U.S. Pat. No. 4,658,019; European Patent Application No. 501,233, published Sep. 2, 1992, among others]. See, Example 2 below, which employs the commercially available antibody GK1.5 (ATCC Accession No. TIB207) to deplete CD4+ cells. Depletion of CD4+cells is shown to inhibit the CTL elimination of the viral vector.

Alternatively, any agent that interferes with the activation of B cells by $T_H$ cells is useful in the methods of this invention. For example, it is necessary for the activation of B cells by T cells for certain interactions to occur [F. H. Durie et al, *Immunol. Today*, 15(9):406–410 (1994)], such as the binding of CD40 ligand on the T helper cell to the CD40 antigen on the B cell, and the binding of the CD28 and/or CTLA4 ligands on the T cell to the B7 antigen on the B cell. Without both interactions, the B cell cannot be activated to induce production of the neutralizing antibody.

Thus, the method of this invention may be accomplished by use of agents which can block the interactions necessary for B cell activation by T helper cells, and thus neutralizing antibody formation. An agent which blocks the CD40 ligand on the $T_H$ cell interferes with the normal binding of CD40 ligand on the T helper cell with the CD40 antigen on the B cell. Thus, a soluble CD40 molecule or an antibody to CD40 ligand [available from Bristol-Myers Squibb Co; see, e.g., European patent application 555,880, published Aug. 18, 1993] can be a selected immune modulator in this method.

Alternatively, an agent which blocks the CD28 and/or CTLA4 ligands present on T helper cells interferes with the normal binding of those ligands with the antigen B7 on the B cell. Thus, a soluble form of B7 or an antibody to CD28 or CTLA4, e.g., CTLA4-Ig [available from Bristol-Myers Squibb Co; see, e.g., European patent application 606,217, published Jul. 20, 1994] can be the selected immune modulator in this method.

Although less desirable than the above-listed immune modulators, other immune modulators or agents that non-specificly inhibit immune function, i.e., cyclosporin A or cyclophosphamide, may also be useful in this method.

A suitable amount or dosage of the immune modulator will depend primarily on the amount of the recombinant vector bearing the transgene which is initially administered to the patient and the type of immune modulator selected. Other secondary factors such as the condition being treated, the age, weight, general health, and immune status of the patient, may also be considered by a physician in determining the dosage of immune modulator to be delivered to the patient. Generally, for example, a therapeutically effective human dosage of a cytokine immune modulator, e.g., IL-12 or γ-IFN, is generally in the range of from about 0.5 μg to about 5 mg per about $1 \times 10^7$ pfu/ml virus vector. Various dosages may be determined by one of skill in the art to balance the therapeutic benefit against any side effects.

II. Viral Vectors

Suitable viral vectors useful in gene therapy are well known, including retroviruses, vaccinia viruses, poxviruses, adenoviruses and adeno-associated viruses, among others. The method of this invention is anticipated to be useful with any virus which forms the basis of a gene therapy vector. However, exemplary viral vectors for use in the method of the invention are adenovirus vectors [see, e.g., M. S. Horwitz et al, "Adenoviridae and Their Replication", *Virology*, second edition, pp. 1712, ed. B. N. Fields et al, Raven Press Ltd., New York (1990); N. Rosenfeld et al, *Cell*, 68:143–155 (1992); J. F. Engelhardt et al, *Human Genet. Ther.*, 4:759–769 (1993); Y. Yang et al, *Nature Genet.*, 7:362–269 (1994); J. Wilson, *Nature*, 365:691–692 (October 1993); B. J. Carter, in "Handbook of Parvoviruses", ed. P. Tijsser, CRC Press, pp. 155–168 (1990).

Particularly desirable are human type C adenoviruses, including serotypes Ad2 and Ad5, which have been rendered replication defective for gene therapy by deleting the early gene locus that encodes E1a and E1b. There has been much published on the use of E1 deleted adenoviruses in gene therapy. See, K. F. Kozarsky and J. M. Wilson, *Curr. Opin. Genet. Dev.*, 3:499–503 (1993). The DNA sequences of a number of adenovirus types, including type Ad5, are available from Genbank. The adenovirus sequences may be obtained from any known adenovirus type, including the presently identified 41 human types [Horwitz et al, *Virology*, 2d ed., B. N. Fields, Raven Press, Ltd., New York (1990)]. A variety of adenovirus strains are available from the American Type Culture Collection, Rockville, Md., or available by request from a variety of commercial and institutional sources. In the following embodiment an adenovirus, type 5 (Ad5) is used for convenience.

The selection of the virus for the recombinant vectors useful in this method, including the viral type, e.g., adenovirus, and strain are not anticipated to limit the following invention.

Similarly, selection of the transgene contained within the viral vector is not a limitation of this invention. This method is anticipated to be useful with any transgene. Suitable transgenes for delivery to a patient in a viral vector for gene therapy are known to those of skill in the art. These therapeutic nucleic acid sequences typically encode products for administration and expression in a patient in vivo or ex vivo to replace or correct an inherited or non-inherited genetic defect or treat an epigenetic disorder or disease. Such therapeutic genes which are desirable for the performance of gene therapy include, without limitation, a very low density lipoprotein gene (VLDL) for the treatment of familial hypercholesterolemia or familial combined hyperlipidemia, the cystic fibrosis transmembrane regulator gene (CFTR) for treatment of cystic fibrosis, DMD Becker allele for treatment of Duchenne muscular dystrophy, and a number of genes which may be readily selected by one of skill in the art. Thus, the selection of the transgene is not considered to be a limitation of this invention, as such selection is within the knowledge of the art-skilled.

The viral vector bearing a therapeutic gene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The viral vector is administered in sufficient amounts to transfect the desired cells and provide sufficient levels of transduction and expression of the selected transgene to provide a therapeutic benefit without undue adverse or with medically acceptable physiological effects which can be determined by those skilled in the medical arts. Conventional and pharmaceutically acceptable routes of administration include direct delivery to the target organ, tissue or site, intranasal, intravenous, intramuscular, subcutaneous, intradermal, oral and other parental routes of administration. Routes of administration may be combined, if desired.

Dosages of the viral vector will depend primarily on factors such as the condition being treated, the selected gene, the age, weight and health of the patient, and may thus vary among patients. For example, a therapeutically effective human dosage of the viral vectors is generally in the range of from about 20 to about 50 ml of saline solution containing concentrations of from about $1 \times 10^7$ to $1 \times 10^{10}$ pfu/ml viruses. A preferred adult human dosage is about 20 ml saline solution at the above concentrations. The dosage will be adjusted to balance the therapeutic benefit against any side effects. The levels of expression of the selected gene can be monitored to determine the selection, adjustment or frequency of dosage administration.

III. The Method of the Invention

The method of this invention involves the co-administration of the selected immune modulator with the selected recombinant viral vector. The co-administration occurs so that the immune modulator and vector are administered within a close time proximity to each other. It is presently preferred to administer the modulator concurrently with or no longer than one day prior to the administration of the vector. The immune modulator may be administered separately from the recombinant vector, or, if desired, it may be administered in admixture with the recombinant vector.

For example, where a cytokine, e.g., IL-12 and/or γIFN, is the immune modulator, the modulators are desirably administered in close time proximity to the administration of the viral vector used for gene therapy. Particularly, the inventors have found that administration of IL-12 or γIFN causes reduction in $T^H 2$ cell levels for about 2–3 days. Therefore, IL-12 and/or γIFN are desirably administered within a day of the administration of the viral vector bearing the gene to be delivered. Preferably, however, the IL-12 and/or γIFN are administered essentially simultaneously with the viral vector.

The immune modulator may be administered in a pharmaceutically acceptable carrier or diluent, such as saline. For example, when formulated separately from the viral vector, the immune modulator, such as IL-12 and/or γ-IFN, is desirably suspended in saline solution. Such a solution may contain conventional components, e.g. pH adjusters, preservatives and the like. Such components are known and may be readily selected by one of skill in the art.

Alternatively, the immune modulator may be itself administered as DNA, either separately from the vector or admixed with the recombinant vector bearing the transgene. Methods exist in the art for the pharmaceutical preparation of the modulator as protein or as DNA [See, e.g., J. Cohen, Science, 259:1691–1692 (1993) regarding DNA vaccines]. Desirably the immune modulator is administered by the same route as the recombinant vector.

The immune modulator, e.g., IL-12 or γIFN, may be formulated directly into the composition containing the viral vector administered to the patient. Alternatively, the immune modulator, may be administered separately, preferably shortly before or after administration of the viral vector. In another alternative, a composition containing one immune modulator, such as IL-12, may be administered separately from a composition containing a second immune modulator, such as γIFN, and so on depending on the number of immune modulators administered. These administrations may independently be before, simultaneously with, or after administration of the viral vector.

The administration of the selected immune modulator may be repeated during the treatment with the recombinant adenovirus vector carrying the transgene, during the period of time that the transgene is expressed, as monitored by assays suitable to the transgene or its intended effect) or with every booster of the recombinant vector. Alternatively, each reinjection of the same viral vector may employ a different immune modulator.

One advantage of the method of this invention is that it represents a transient manipulation, necessary only at the time of administration of the gene therapy vector, and it is anticipated to be safer than strategies based on induction of tolerance which may permanently impair the ability of the recipient to respond to adenovirus infections. Furthermore, the use of immune modulators such as the above-mentioned cytokines or antibodies in preference to agents such as cyclosporin or cyclophosphamide is anticipated to be safer than generalized immune suppression because the transient immune modulation is selective (i.e., CTL mediated responses are retained as are humoral responses dependent on $T_H1$ function).

In one example of efficient gene transfer according to the method of this invention, the selected immune modulators are IL-12, which causes the selective induction of $T_H1$ cells, and/or γIFN, which suppresses induction of $T_H2$ cells. Another immune modulator is the anti-CD4+ antibody, GK1.5, which depletes the $T_{H1}$ cells, and reduces CTL elimination of the vector. In conjunction with gene therapy which utilized an adenovirus vector containing either an alkaline phosphatase ("Alk") transgene or a beta-galactosidase ("lacZ") transgene, the use of these immune modulators permitted efficient gene transfer, as well as repeated use of the same viral vector.

As detailed in Example 2 below, animals were injected with IL-12 at the time of the first administration of a recombinant adenovirus vector. Analysis of lymphocytes stimulated in vitro with virus revealed an increased secretion of IL-2 and IFN-γ and a relative decreased production of IL-4 as compared to animals that did not receive IL-12 (i.e., ratio of IL2/IL-4 was increased from 3 to 6 when IL-12 was used). More importantly, IL-12 selectively blocked secretion of antigen specific IgA without significantly impacting on formation of IgG; this was concurrent with a 100-fold reduction in neutralizing antibody. High level gene transfer to airway epithelial cells was achieved when the adenovirus vector was readministered to IL-12 treated animals.

Similar experiments were also performed with IFN-γ which is believed to mediate many of the biological effects of IL-12 via secretion of activated macrophages and T helper cells. Mice were injected with IFN-γ using the IL-12 dosing regimen. These animals were virtually indistinguishable from the animals treated with IL-12 in that virus specific IgA and neutralizing antibody was decreased 100-fold as compared to animals not treated with cytokine and efficient gene transfer was accomplished upon a second administration of virus.

In the same experiments, depletion of the CD4+ cells were shown to effectively permit readministration of the vector without immediate CTL elimination.

The following examples illustrate the preferred methods for preparing suitable viral vectors useful in the gene therapy methods of the invention. These examples are illustrative only and do not limit the scope of the invention.

EXAMPLE 1

Construction and Purification of Exemplary Recombinant Adenovirus Vectors

The recombinant adenovirus, H5.010CMVLacZ, was constructed as follows. The plasmid pAd.CMVlacZ [described in Kozarsky et al, J. Biol. Chem., 269(18):13695–13702 (1994)], which contains adenovirus map units 0–1, followed by a cytomegalovirus enhancer/promoter [Boshart et al, Cell, 41:521–530 (1985)], an E. coli beta-galactosidase gene (lacZ), a polyadenylation signal (pA), adenovirus 5 map units 9–16 (Ad 9–16) and generic plasmid sequences including an origin of replication and ampicillin resistance gene was used. pAd.CMVlacZ was linearized with NheI and co-transfected into 293 cells [ATCC CRL1573] with sub360 DNA (derived from adenovirus type 5) which had been digested with XbaI and ClaI as previously described [K. F. Kozarsky, Somatic Cell Mol. Genet., 19:449–458 (1993) and Kozarsky (1994), cited above]. The resulting recombinant virus H5.010CMVLacZ contains adenovirus map units 0–1, followed by a CMV enhancer/promoter, a lacZ gene, a polyadenylation signal (pA), adenovirus map units 9–100, with a small deletion in the E3 gene.

The recombinant adenovirus, H5.010CBALP, contains the adenovirus map units 0–1, followed by a CMV enhanced, chicken cytoplasmic β-actin promoter [T. A. Kost et al, Nucl. Acids Res., 11(23):8287 (1983)], a human placental alkaline phosphatase gene, a polyadenylation signal (pA), and adenovirus type 5 map units 9–100, with a small deletion in the E3 gene (the Ad 5 sub360 backbone). This recombinant adenovirus was constructed substantially similarly to the H5.010CMVLacZ described above. See, also, Kozarsky (1994), cited above.

These recombinant adenoviruses, H5.010CMVLacZ and H5.010CBALP, were isolated following transfection [Graham, Virol., 52:456–467 (1974)], and were subjected to two rounds of plaque purification. Lysates were purified by cesium chloride density centrifugation as previously described [Englehardt et al, Proc. Natl. Acad. Sci. USA, 88:11192–11196 (1991)]. Cesium chloride was removed by passing the virus over a BioRad DG10 column using phosphate-buffered saline.

For mouse experiments, virus was either used fresh, or after column purification, glycerol was added to a final concentration of 10% (v/v), and virus was stored at −70° C. until use.

EXAMPLE 2

Enhancement of Adenovirus Mediated Gene Transfer upon Second Administration by IL-12 and IFN-γ in Mouse Lung.

The recombinant adenoviruses H5.010CMVlacZ and H5.010CBALP were used in this example. Each virus expresses a different reporter transgene whose expression can be discriminated from that of the first reporter transgene.

Female C57BL/6 mice (6~8 week old) were infected with suspensions of H5.010CBALP (1×10$^9$ pfu in 50 µl of PBS) via the trachea at day 0 and similarly with H5.010CMVlacZ at day 28. One group of such mice was used as a control. Another group of mice were acutely depleted of CD4$^+$ cells by i.p. injection of antibody to CD4$^+$ cells (GK1.5; ATCC No. TIB207, 1:10 dilution of ascites) at the time of the initial gene therapy (days −3, 0, and +3). A third group of mice were injected with IL-12 (1 µg intratracheal or 2 µg, i.p. injections) at the time of the first administration of virus (days 0 and +1). A fourth group of mice were injected with gamma interferon (1 µg intratracheal or 2 µg, i.p. injections) at the time of the first administration of virus (days 0 and +1).

When mice were subsequently euthanized and necropsied at days 3, 28, or 31, lung tissues were prepared for cryosections, while bronchial alveolar lavage (BAL) and mediastinal lymph nodes (MLN) were harvested for immunological assays.

A. Cryosections

The lung tissues were evaluated for alkaline phosphatase expression by histochemical staining following the procedures of Y. Yang et al, cited above. The results are depicted in FIGS. 1A–1L.

Instillation of alkaline phosphatase virus (10$^9$ pfu) into the airway of all groups of the C57BL/6 mice resulted in high level transgene expression in the majority of conducting airways that diminishes to undetectable levels by day 28. Loss of transgene expression was shown to be due to CTL mediated elimination of the genetically modified hepatocytes [Y. Yang et al, cited above].

In the control mice, no recombinant gene expression was detected three days after the second administration of virus, i.e., day 31.

Administration of virus to the CD4+ depleted animals was associated with high level recombinant transgene expression that was stable for a month (FIGS. 1D–1F). Expression of the second virus was detectable on day 31.

Initial high level gene transfer diminished after about one month in the IL-12 treated mice; however, in contrast to the control, high level gene transfer to airway epithelial cells was achieved when virus was readministered to IL-12 treated animals at day 28, as seen in the day 31 results (FIGS. 1G–1I).

The gamma-interferon treated animals were virtually indistinguishable from the animals treated with IL-12 in that efficient gene transfer was accomplished upon a second administration of virus (FIGS. 1J–1L).

Thus, the use of these cytokines as immune modulators enabled the repeated administration of the vector without its immediate elimination by neutralizing antibody.

B. Immunological Assays—MLN

Lymphocytes from MLN of the control group and IL-12 treated group of C57BL/6 mice harvested 28 days after administration of H5.010CBALP were restimulated in vitro with UV-inactivated H5.010CMVlacZ at 10 particles/cell for 24 hours. Cell-free supernatants were assayed for the presence of IL-2 or IL-4 on HT-2 cells (an IL-2 or IL-4-dependent cell line) (Y. Yang et al, cited above]. Presence of IFN-γ in the same lymphocyte culture supernatant was measured on L929 cells as described [Y. Yang et al, cited above]. Stimulation index (S.I.) was calculated by dividing $^3$H-thymidine cpm incorporated into HT-2 cells cultured in supernatants of lymphocytes restimulated with virus by those incorporated into HT-2 cells cultured in supernatants of lymphocytes incubated in antigen-free medium.

The results are shown in Table 1 below.

TABLE 1

| | $^3$H-Thymidine Incorporation (cmp ± SD) | | IFN-γ liter | |
|---|---|---|---|---|
| | Medium | H5.010CMVlacZ | S.I. | (IU/ml)$^d$ |
| C57BL/6 | 175 ± 40 | 2084 ± 66 | 11.91 | 80 |
| anti-IL2 (1:5000) | | 523 ± 81 | 2.98 | |
| anti-IL4 (1:5000) | | 1545 ± 33 | 8.83 | |
| C57BL/6 + IL12 | 247 ± 34 | 5203 ± 28 | 21.07 | 160 |
| anti-IL2 (1:5000) | | 776 ± 50 | 3.14 | |
| anti-IL4 (1:5000) | | 4608 ± 52 | 18.66 | |

Stimulation of lymphocytes from regional lymph nodes with both recombinant adenoviruses led to secretion of cytokines specific for the activation of both $T_{H1}$ (i.e., IL-2 and IFN-γ) and $T_{H2}$ (i.e., IL-4) subsets of T helper cells (Table 1).

Analysis of lymphocytes from the IL-12 treated animals stimulated in vitro with virus revealed an increased secretion of IL-2 and IFN-γ and a relative decreased production of IL-4 as compared to animals that did not receive IL-12 (i.e., ratio of IL-2/IL-4 was increased from 3 to 6 when IL-12 was used; Table 1).

C. Immunological Assays—BAL

BAL samples obtained from animals 28 days after primary exposure to recombinant virus were evaluated for neutralizing antibodies to adenovirus and anti-adenovirus antibody isotypes as follows. The same four groups of C57BL/6 mice, i.e., control, CD4$^+$ depleted, IL-12 treated and IFN-γ treated, were infected with H5.010CBALP. Neutralizing antibody was measured in serially diluted BAL samples (100 µl) which were mixed with H5.010CBlacZ (1×10$^6$ pfu in 20 µl), incubated for 1 hour at 37° C., and applied to 80% confluent Hela cells in 96 well plates (2×10$^4$ cells per well). After 60 minutes of incubation at 37° C., 100 µl of DMEM containing 20% FBS was added to each well. Cells were fixed and stained for β-galactosidase expression the following day.

All cells were lacZ positive in the absence of anti-adenoviral antibodies.

Adenovirus-specific antibody isotype was determined in BAL by using enzyme-linked immunosorbent assay (ELISA). Briefly, 96-well plates were coated with 100 µl of PBS containing 5×10$^9$ particles of H5.010CBlacZ for 18 hours at 4° C. The wells were washed 5 times with PBS. After blocking with 200 µl of 2% BSA in PBS, the plates were rinsed once with PBS and incubated with 1:10 diluted BAL samples for 90 minutes at 4° C. Thereafter, the wells were extensively washed and refilled with 100 µl of 1:1000 diluted alkaline phosphatase-conjugated anti-mouse IgG or IgA (Sigma). The plates were incubated, subsequently washed 5 times, and 100 µl of the substrate solution (p-nitrophenyl phosphate, PNPP) was added to each well. Substrate conversion was stopped by the addition of 50 µl of 0.1M EDTA. Plates were read at 405 nm.

Figure 2B:
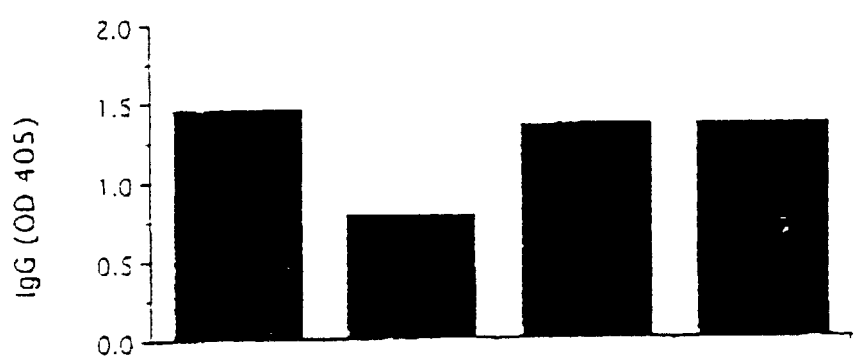
FIG. 2B is a graph summarizing the relative amounts (OD$_{405}$) of IgG present in BAL samples. The symbols are as described in FIG. 2A.
Figure 2C:
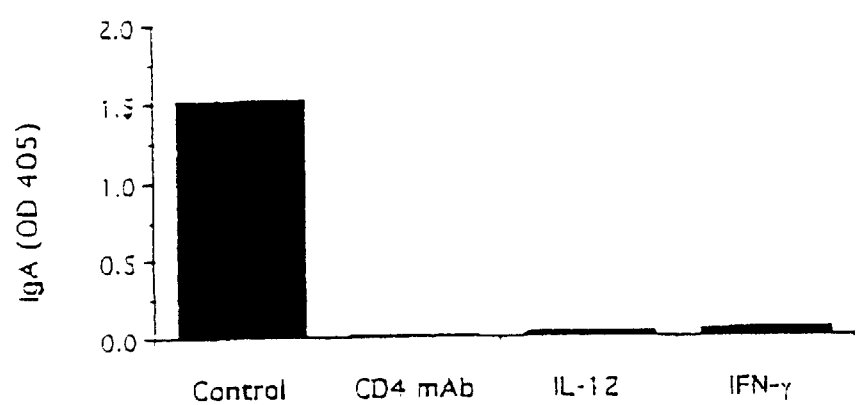
FIG. 2C is a graph summarizing the relative amounts (OD$_{405}$) of IgA present in BAL samples. The symbols are as described in FIG. 2A.

The results are shown graphically in FIGS. 2A through 2C, which summarize neutralizing antibody titer, and the relative amounts (OD$_{405}$) of IgG and IgA present in BAL samples. The titer of neutralizing antibody for each sample was reported as the highest dilution with which less than 50% of cells stained blue.

As demonstrated in the first bar of FIGS. 2A through 2C, the cytokines identified in Table 1 above were associated in the control mice with the appearance of antibodies to adenovirus proteins in BAL of both the IgG and IgA isotypes that were capable of neutralizing the human Ad5 recombinant vector in an in vitro assay out to a 1:800 dilution.

As shown in the second bar of the graphs of FIGS. 2A through 2C, transient CD4$^+$ cell depletion inhibited the formation of neutralizing antibody (FIG. 2A) and virus specific IgA antibody (FIG. 2C) by 80-fold, thereby allowing efficient gene transfer to occur following a second administration of virus (see FIG. 2F). FIG. 2B shows a slight inhibition of IgG as well.

As shown in the third bar of the three graphs, IL-12 selectively blocked secretion of antigen specific IgA (FIG. 2C), without significantly impacting on formation of IgG (FIG. 2B). This was concurrent with a 32-fold reduction in neutralizing antibody (FIG. 2A).

The gamma-interferon treated animals (fourth bar of FIGS. 2A through 2B) were virtually indistinguishable from the animals treated with IL-12 in that virus specific IgA (FIG. 2C) and neutralizing antibody (FIG. 2A) were decreased as compared to the control animals not treated with cytokine, but not to the extent obtained with those treated with IL-12.

These studies demonstrate that the administration of selected immune modulators to recipients of gene therapy recombinant viral vectors at or about the time of primary exposure to the vector can prevent the formation of blocking antibodies and/or CTL elimination of the vector both initially and at the time of repeated exposure to the viral vector. The concordant reduction of neutralizing antibody with antiviral IgA suggests that immunoglobulin of the IgA subtype is primarily responsible for the blockade to gene transfer.

EXAMPLE 3

Enhancement of Adenovirus mediated Gene Transfer upon Second Administration by IL-12 and IFN-γ in Mouse Liver Experiments substantially identical to those described in Example 2 above were conducted in which the location of administration of the viral vectors was the blood for introduction of the transgene into the liver, vs. the lung.

The recombinant adenoviruses H5.010CMVlacZ and H5.010CBALP were used in this example.

Female C57BL/6 mice (6~8 week old) were injected with suspensions of H5.010CBALP (1×10$^9$ pfu in 50 µl of PBS) i.p. at day 0 and similarly with H5.010CMVlacZ at day 28. One group of such mice was used as a control. Another group of mice were acutely depleted of CD4$^+$ cells by i.p. injection of antibody to CD4$^+$ cells (GK1.5; ATCC No. TIB207, 1:10 dilution of ascites) at the time of the initial gene therapy (days −3, 0, and +3). A third group of mice were injected with IL-12 (2 µg, i.p. injections) at the time of the first administration of virus (days 0 and +1). A fourth group of mice were injected with gamma interferon (2 µg, i.p. injections) at the time of the first administration of virus (days 0 and +1).

When mice were subsequently euthanized and necropsied at days 3, 28, or 31, liver tissues were prepared for cryosections according to the procedures used above for lung tissue in Example 2.

A. Cryosection Results

The results were substantially similar for liver-directed gene therapy according to this method as for the lung-directed therapy of Example 2 above.

Administration of alkaline phosphatase virus (10$^9$ pfu) into the veins of all groups of the C57BL/6 mice resulted in high level transgene expression in liver tissue that diminishes to undetectable levels by day 28. Loss of transgene expression was shown to be due to CTL mediated elimination of the genetically modified hepatocytes [Y. Yang et al, cited above].

In the control mice, no recombinant gene expression was detected three days after the second administration of virus, i.e., day 31.

Administration of virus to the CD4+ depleted animals was associated with substantially lower neutralizing antibodies and high level recombinant transgene expression that was stable for a month. Expression of the second virus was detectable on day 31.

Initial high level gene transfer diminished after about one month in the IL-12 treated mice; however, in contrast to the control, some gene transfer to the liver via the blood was achieved when virus was readministered to IL-12 treated animals at day 28 and the level of neutralizing antibody was reduced.

The gamma-interferon treated animals were virtually indistinguishable from the animals treated with IL-12 in that efficient gene transfer was accomplished upon a second administration of virus.

Thus, the use of these cytokines and the anti-CD4+ antibodies as immune modulators enabled the repeated liver-directed administration of the vector without its immediate elimination by neutralizing antibody.

All articles identified herein are incorporated by reference. Numerous modifications and variations of the present invention are included in the above-identified specification and are expected to be obvious to one of skill in the art. Such modifications and alterations including the specific immune modulator selected, the manner of administration, the recombinant vector and transgene selected, route of administration, etc. are believed to be encompassed in the scope of the claims appended hereto.

What is claimed is:

1. A method of inhibiting in a mammal formation of neutralizing antibodies directed against a recombinant adenovirus comprising the step of co-administering to said mammal said adenovirus and an antibody directed against CD4, wherein formation of neutralizing antibodies is inhibited.

2. The method according to claim 1, further comprising the step of re-administering the adenovirus.

3. The method according to claim 1, wherein CTL killing of virally infected cells is reduced.

4. The method according to claim 1, wherein said antibody directed against CD4 is administered simultaneously with said adenovirus.

5. The method according to claim 1, wherein said antibody directed against CD4 is administered prior to administration of said adenovirus.

6. The method according to claim 1, wherein said antibody directed against CD4 is administered subsequently to administration of said adenovirus.

7. A method of inhibiting in a mammal formation of neutralizing antibodies directed against a recombinant adenovirus comprising the step of co-administering to said mammal said adenovirus and interleukin-12, wherein formation of neutralizing antibodies is inhibited.

8. The method according to claim 7, further comprising the step of re-administering said adenovirus.

9. The method according to claim 7, wherein said interleukin-12 is administered simultaneously with said adenovirus.

10. The method according to claim 7, wherein said interleukin-12 is administered prior to administration of said adenovirus.

11. The method according to claim 7, wherein said interleukin-12 is administered subsequently to administration of said adenovirus.

12. A method of inhibiting in a mammal formation of neutralizing antibodies directed against a recombinant adenovirus comprising the step of co-administering to said mammal said adenovirus and interferon-gamma, wherein formation of neutralizing antibodies is inhibited.

13. The method according to claim 12, further comprising the step of re-administering said adenovirus.

14. The method according to claim 12, wherein said interferon-gamma is administered simultaneously with said adenovirus.

15. The method according to claim 12, wherein said interferon-gamma is administered prior to administration of said adenovirus.

16. The method according to claim 12, wherein said interferon-gamma is administered subsequently to administration of said adenovirus.

17. A method of inhibiting in a mammal formation of neutralizing antibodies directed against a recombinant adenovirus comprising the step of co-administering to said mammal said adenovirus and an antibody directed against CD40 ligand, wherein formation of neutralizing antibodies is inhibited.

18. The method according to claim 17, further comprising the step of re-administering said adenovirus.

19. The method according to claim 17, wherein said antibody directed against CD40 ligand is administered simultaneously with said adenovirus.

20. The method according to claim 17, wherein said antibody directed against CD40 ligand is administered prior to administration of said adenovirus.

21. The method according to claim 17, wherein said antibody directed against CD40 ligand is administered subsequently to administration of said adenovirus.

* * * * *

UNITED STATES PATENT AND TRADEMARK OFFICE
CERTIFICATE OF CORRECTION

PATENT NO. : 5,872,154
DATED : February 16, 1999
INVENTOR(S) : James M. Wilson, Yiping Yang, and Giorgio Trinchieri It is certified that error appears in the above-identified patent and that said Letters Patent is hereby corrected as shown below:

Col. 1, line 6, replace "39412-02" with --3412-02--.

Col. 4, line 5, replace "1:1047" with --152:1047--.

Col. 6, line 54, replace "T$^H$2" with --T$_H$2--.

Col. 10, in Table 1, in the first heading, replace "cmp" with --cpm--.

Col. 12, Claim 2, line 43, before "adenovirus", replace "the" with --said--.

Signed and Sealed this

Seventeenth Day of August, 1999

Attest:

Q. TODD DICKINSON

*Attesting Officer*  *Acting Commissioner of Patents and Trademarks*